United States Patent [19]

Agarwala et al.

[11] Patent Number: 4,994,159
[45] Date of Patent: Feb. 19, 1991

[54] METHOD AND APPARATUS FOR MEASURING CORROSION BENEATH THIN FILMS

[75] Inventors: Vinod S. Agarwala, Warminster; Paul J. Kennedy, Bensalem, both of Pa.

[73] Assignee: The United States of America as represented by the Secretary of the Navy, Washington, D.C.

[21] Appl. No.: 468,560

[22] Filed: Jan. 23, 1990

[51] Int. Cl.⁵ .............................................. G01N 27/26
[52] U.S. Cl. .................................. 204/153.1; 204/404
[58] Field of Search ............................. 204/153.1, 404

[56] References Cited

U.S. PATENT DOCUMENTS 4,488,939 12/1984 Fu ........................................ 204/404
4,784,729 11/1988 Jasinski ............................. 204/153.1

*Primary Examiner*—John F. Niebling
*Assistant Examiner*—Steven P. Marquis
*Attorney, Agent, or Firm*—James V. Tura; James B. Bechtel; Susan E. Verona

[57] ABSTRACT

A method and an apparatus are provided which can quantitatively measure the corrosion-inhibiting ability of thin films of materials such as lubricants. A galvanic cell is created on a sensitive surface using alternating layers of anodic and cathodic materials such as steel and copper, which are electrically isolated by an insulation matrix. The surface is then coated with a film of the material to be tested which is then allowed to drain therefrom. The surface is then cooled to below the dew point of the surrounding environment to cause condensation on the thin film. The galvanic current between the anodic and cathodic materials is then monitored for the first indication of environmental penetration through the film, i.e., corrosion.

25 Claims, 2 Drawing Sheets

METHOD AND APPARATUS FOR MEASURING CORROSION BENEATH THIN FILMS

STATEMENT OF GOVERNMENT INTEREST

The invention described herein may be manufactured and used by and for the Government of the United States of America for governmental purposes without the payment of any royalties thereon or therefor.

BACKGROUND OF THE INVENTION

This invention relates generally to a method and an apparatus for measuring corrosion and more particularly to a method and an apparatus for measuring the corrosion beneath thin films of material.

The destructive effects of corrosion are well known and efforts to minimize those effects are ongoing. The naval aircraft-carrier environment is a particularly corrosive one, with sulfur from aircraft-carrier stack gases combining with sea spray to provide a hostile environment which undermines the structural integrity of naval aircraft. Corrosion of aircraft hydraulic pistons, engine components, and bearings is a particularly serious problem. The corrosion protection of such parts relies greatly on the formation and stability of thin lubricant films which remain on the metal surfaces after the lubricant drains, and act as barriers to the hostile environment. The corrosion-inhibiting ability of these thin lubricant films is therefore of considerable importance. For example, naval aircraft turbine engine bearings have exhibited severe corrosion problems due to the harsh aircraft-carrier environment and have relied on lubricant for corrosion protection. Work has been done in the area of developing lubricant oils for these bearings which have the necessary thermal stability for such a high temperature application without sacrificing good corrosion-inhibiting ability. Efforts have also been made to develop additives to make existing oils more corrosion-inhibitive. Means are necessary for testing the effectiveness of these new lubricants as corrosion inhibitors. Such a testing means would be useful in testing lubricants for other applications such as automobiles, as well as in testing other liquid films as corrosion inhibitors.

The traditional method of measuring the corrosion-inhibiting ability of a lubricant consists of placing a lubricant-coated specimen in a standard humidity cabinet and measuring the amount of time required for formation of one or more rust spots. Another commonly used method is to expose lubricant-covered or painted metal panels to tropical or sea environments and then to measure the length of time required for initiation of visible corrosion. These methods lack good reproducibility and are not quantitative. They also rely on visual identification of spots, whereas corrosion is actually present before it becomes visible.

A more recent development in measuring the corrosion-inhibiting characteristics of lubricants involves suspending a lubricant-coated steel test specimen over boiling acidified water and measuring the weight change in the specimen as a function of hours of exposure. Although this method is quantitative, the corrosive test conditions represent an acidic type of corrosion process not reflective of the type of corrosion which actually occurs in typical marine or tropical environments. These methods also lack sufficient sensitivity to detect the slight changes in corrosion rates that occur in response to changes in environmental conditions.

Galvanic cell-type corrosion probes are currently used to determine the corrosivity of a surrounding medium. Such probes have been used on naval aircraft carriers to monitor the corrosivity of the sea environment due to moisture and salt and are used in the absence of any protective films. In operation, a thin film of water from the environment in question, usually in the form of sea spray, contacts the bare probe, acting as an electrolyte to complete the galvanic cell formed by two dissimilar metals in the bare probe separated by insulation. In other words, this film of water acts as a pathway for current flow between the surfaces of the dissimilar metals. Such probes have only been used bare and only to measure the corrosivity of the environment. Their use for measuring the corrosion-inhibiting abilities of coatings has not been contemplated, nor are they structurally suitable for such use.

SUMMARY OF THE INVENTION

It is therefore an object of the present invention to provide a method and an apparatus that can quantitatively measure the corrosion-inhibiting abilities and corrosivity of thin films of materials such as lubricants and paints.

It is another object to provide a highly sensitive such apparatus which exhibits good reproducibility of test results.

It is a more particular object to provide a method and an apparatus which will detect the initiation of corrosion even before it is visible.

Another object is to provide a probe with enhanced sensitivity which does not require an aggressive artificial environment to product a measurable amount of corrosion or oxidation and can therefore be used in an environment that more accurately reflects where the material is actually used.

Still another object is to provide a method of testing lubricants which simulates the actual drainage conditions in which the lubricants are used.

Yet another object is to provide a method and an apparatus which are sufficiently sensitive to detect slight changes in corrosion rates beneath films.

Briefly, these and other objects of the invention are accomplished by a method and an apparatus which can monitor the corrosion beneath thin films of materials such as lubricants and paints. A galvanic cell is created on a sloped sensitive surface between electrically isolated surface areas of anodic and cathodic material. The surface is then coated with a film of the material to be tested which is then allowed to drain therefrom, and then cooled to below the dew point of the surrounding environment to cause condensation on the film. The galvanic current between the anodic and cathodic materials is then monitored for the first indication of environmental penetration through the film, i.e., corrosion.

These and other objects, advantages, and novel features of the invention will become apparent from the following detailed description of the invention when considered in conjunction with the accompanying drawings wherein:

DESCRIPTION OF THE PREFERRED EMBODIMENT

The present invention provides a method and apparatus for determining the corrosion-inhibiting properties and the corrosivity of thin films of materials such as lubricants, hydraulic fluids, greases, and solid films. The method and apparatus are based on the measurement of the corrosion current generated electrochemically by a galvanic cell beneath the thin film. This current is directly related to the film's effectiveness in preventing corrosion and, in some cases, its tendency to cause corrosion.

Figure 1:
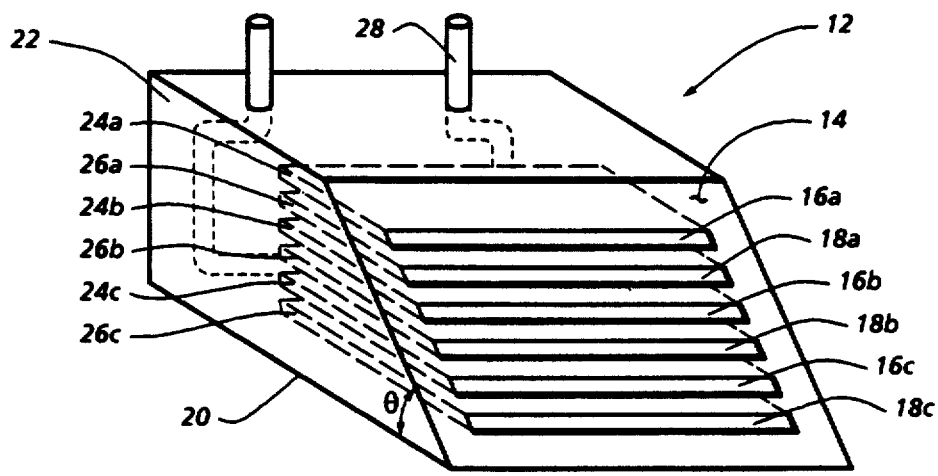
FIG. 1 is a diagrammatic view of the probe of the corrosion-monitoring apparatus of the present invention.
Figure 2:
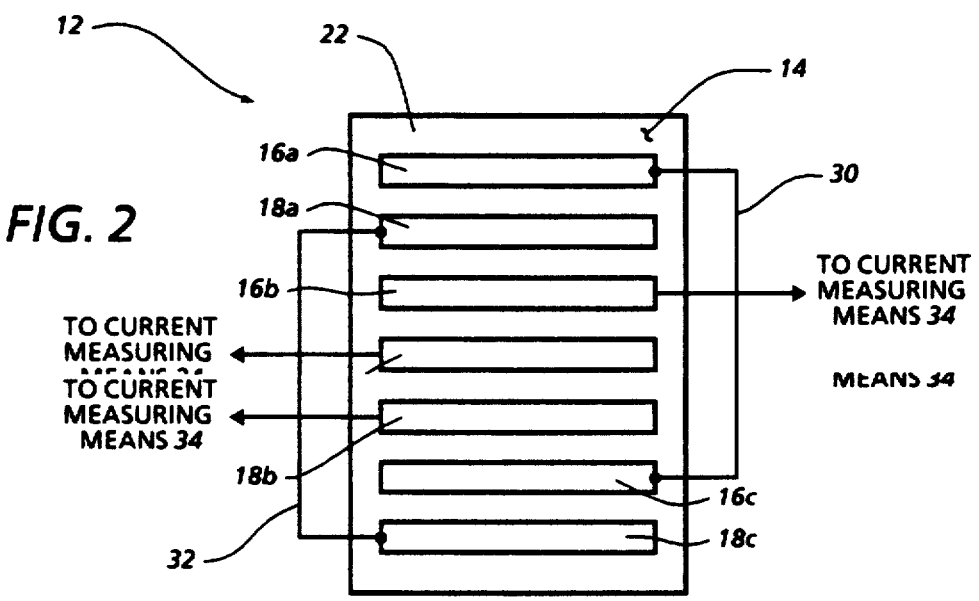
FIG. 2 is a diagrammatic view of the sensitive face of the probe shown in FIG. 1.
Figure 3:
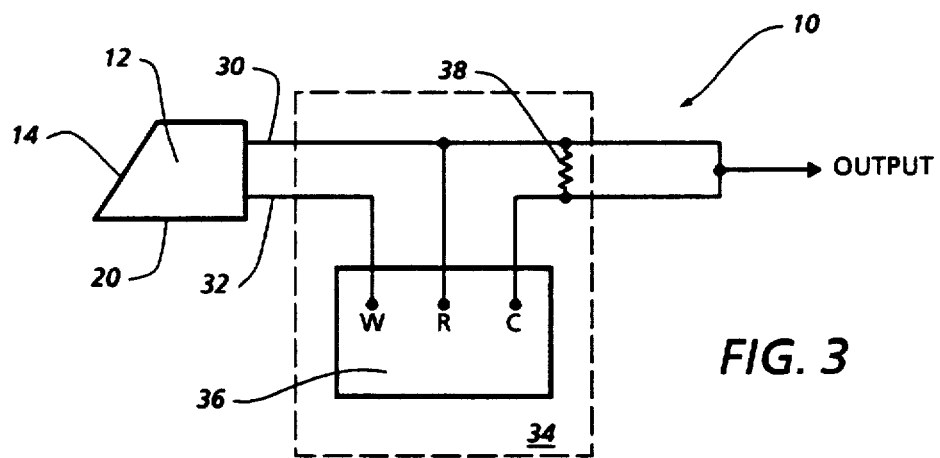
FIG. 3 is a diagrammatic view of the corrosion monitoring apparatus of the present invention showing the current measuring means.

Referring now to the drawings wherein like characters designate like or corresponding parts throughout the several views, there is shown in FIGS. 1, 2, and 3 a corrosion-monitoring apparatus 10 of the present invention. Essentially, the apparatus 10 provides a probe 12 having an essentially flat sensitive surface or face 14 on which the film, such as lubricant, (not shown) to be tested is disposed. Sensitive face 14 is configured so as to expose thereon electrically isolated surface areas 16 and 18 of an anodic and a cathodic material, respectively, so that when the lubricant is disposed thereon and exposed to a corrosive environment, current is generated between the two materials when corrosion occurs. Under these circumstances, to the extent that the lubricant fails to inhibit corrosion, condensation from the corroding environment breaks through or penetrates the lubricant and comes into contact with sensitive face 14, acting as an electrolyte, or combines with the lubricant to form an emulsion which acts as an electrolyte, creating a galvanic cell between the anodic and cathodic materials. The magnitude of the corrosion current thus generated directly relates to the amount of oxidation occurring at sensitive face 14. The current value and the known value of anodic surface area 16 can be used to calculate the amount in mass of anode corroding. Further manipulation of known data provides the corrosion rate in mass per surface area of anodic material corroding and the corrosion rate over time.

Sensitive face 14 is best configured to achieve this purpose by orienting a plurality, for example 3, of long narrow strips 16a-16c of anodic surface area 16 in alternating relationship with a plurality, for example 3, of long narrow strips 18a-18c of cathodic surface area 18. Strips 16a-16c and 18a-18c are electrically isolated each from the others and are preferably parallel to one another and also to the horizontal. The spacing between adjacent strips of surface areas 16 and 18 should be close enough to permit droplets of electrolyte to bridge the gap therebetween. A distance of about 0.8 mm has been found to be effective. Sensitive face 14 should desirably have a highly smooth surface to minimize the effect of rough spots in accelerating the breakdown of the film. For example, preparing face 14 by hand polishing it with 360- and 600-grade silicon nitride paper followed by alcohol cleaning provides sufficient smoothness.

Probe 12 is configured so that sensitive face 14 slopes to form an angle with the horizontal ranging from 10 to 80 degrees, preferably about 60 degrees, permitting drainage of the lubricant from the face. This feature simulates the actual conditions under which the lubricant is providing corrosion protection on parts such as aircraft turbine engines and automobiles and also provides consistency of film thickness and better reproducibility of test results. Probe 12 may also have a horizontal resting surface 20.

In the preferred embodiment, probe 12 comprises a matrix 22 of insulating material which electrically isolates the anodic and cathodic materials. Embedded within matrix 22 are a plurality, for example three, of plates 24a-24c of anodic material. Each anodic plate 24 is electrically isolated from the others by being completely surrounded by matrix 22, except one edge of each anodic plate, which forms one each of strips 16a, 16b, and 16c of surface area 16 on sensitive face 14.

Also embedded within matrix 22 are a plurality, for example 3, of plates 26a-26c of cathodic material. Cathodic plates 26 are in an alternating relationship with anodic plates 24. Each cathodic plate 26 is electrically isolated from the other cathodic plates and anodic plates 24 by being completely surrounded by matrix 22, except one edge of each cathodic plate, which forms one each of strips 18a, 18b, and 18c of surface area 18 on sensitive face 14.

The selection of anodic and cathodic materials is governed by their relative electrochemical potentials. The greater the electrochemical potential difference the greater the corrosion in a given environment. A preferred anode-cathode combination is an iron alloy coupled with a copper alloy, respectively.

The insulating material of matrix 22 may be any good insulator which is water-impenetrable and forms a good bond with plates 24 and 26, to prevent seepage of the lubricant or electrolyte between the plates. For example, matrix 22 may be an epoxy or may be cloth impregnated with an epoxy. To provide the spacing between plates 24 and 26, the matrix may also comprise teflon plates (not shown) embedded in the epoxy and positioned in alternating relationship with the plates.

A cooling means 28 may be operatively connected to sensitive face 14 for cooling the face to a temperature below the ambient dew point temperature. Cooling means 28 may be a hollow tube, such as of aluminum, embedded within matrix 22 with the open ends thereof external to the matrix, for carrying liquid therethrough which has a temperature below that of the dew point of the surrounding environment. Any means which will cool sensitive surface 14 so as to cause condensation thereon will suffice. Cooling face 14 accelerates the onset of corrosion as well as provides better reproducibility of test results.

To measure the corrosion current generated between surface areas 16 and 18, plates 24 are each commonly connected to a first conducting means or wire 30 and plates 26 are each commonly connected to a second conducting means or wire 32. Wires 30 and 32 are electrically connected to a means 34 for measuring the current therebetween. Current measuring means 34 may be any means for measuring relatively small amounts of current, the smaller the current that can be measure the more sensitive the device to the first signs of corrosion. For example, as shown in FIG. 3, current measuring means 34 may be a zero resistance ammeter comprising a potentiostat 36 in which the potential between the working (w) and the counter (c) terminals thereof are adjusted to zero. A standard resistance box 38 is connected between the reference (r) and the counter (c) terminals to convert the current into a potential drop for amplification and recording. Current variations of up to three orders of magnitude can be recorded easily with such an arrangement without changing the resistance between the reference (r) and the counter (c) terminals. A 100-kohm resistor is adequate to measure current in the range of 0.01 to 10 mA. Using sensitive measuring means allows current to be measured, indicating the onset of corrosion, long before any visible signs of corrosion would be present.

As stated above, means may be operatively connected to the output of current measuring means 34 for calculating the mass of anodic material corroding by dividing the corrosion current by the known value of anodic surface area 16. Means may also be incorporated for calculating the corrosion rate in mass per surface area of anodic material corroding and for calculating the corrosion rate over time. All such calculating means are known to those skilled in the art.

In operation, probe 12 is best used in a controlled environment such as an environmental chamber for good reproducibility of test results. The temperature and humidity in the chamber are adjusted to known or predetermined values, providing it with a known dew point temperature. The lubricant or other thin film of material to be tested (not shown) is coated onto prepared sensitive face 14 and allowed to drain off, simulating the actual conditions under which the lubricant is relied upon to inhibit corrosion. A liquid coolant (not shown) is then circulated through cooling means 28. Condensation then occurs on the surface of the lubricant due to the relative temperatures of the chamber and cooled face 14. Corrosion eventually occurs as the film's ability to provide a barrier between the condensation and sensitive face 14 diminishes, and the condensation breaks through or penetrates the film. Current then begins to flow as the condensation, either alone or in combination with the lubricant, begins to behave as an electrolyte, bridging the gap between adjacent ones of surface areas 16 and 18, creating galvanic cells therebetween. The corrosion current, which correlates directly to the amount of corrosion taking place, is then monitored by current measuring means 34.

Various mineral oils were tested according to the method and the apparatus of the present invention. The particular probe 12 used for the tests was formed from anodic plates 24 of SAE 4130 steel and cathodic plates 26 of copper. Plates 24 and 26 were approximately 140 mm long, 25 mm wide, and 0.8 mm thick. Actual construction involved alternately placing the steel and copper plates 24 and 26 in an aluminum mold so that the final spacing between each was approximately 0.8 mm. After soldering wire leads 30 to each plate 24 and wire leads 32 to each plate 26, the assembly was potted using a two-part epoxy system. The epoxy was built up around the metal plate assembly to form matrix 20, encasing each of plates 24 and 26 therein, but leaving one edge of each exposed on face 14. The soldered end of leads 30 and 32 were also encased in matrix 20. Cooling means 28 was incorporated into probe 12 by encasing a hollow aluminum tube in the epoxy matrix 20 so that both ends of the tube remained external to probe 12. The resulting probe 12 was further shaped to provide the resting surface 20 at a 60-degree angle with sensitive face 14.

Sensitive face 14 of probe 12 was then prepared by hand polishing it with 360- and 600-grade silicon nitride paper, followed by alcohol cleaning. A surface deactivation step then followed that involved coating face 14 with a film of distilled water for 5 minutes, after which the face was towel dried and ready for use.

The current measuring means 34 used was a zero resistance ammeter constructed using a potentiostat 36 (Aardvark Model PEC-1) in which the potential between the working (w) and counter (c) terminals was adjusted to zero. Standard resistance box 38 was connected between the reference (r) and the counter (c) terminals to convert the current into a potential drop for amplification and recording.

The environmental chamber used in the tests was provided with a 100% relative humidity and possibly a certain level of mist by allowing air that was previously heated and saturated with water vapor at an elevated temperature to flow at a rate of 4.5 liters/minute through the chamber. This was achieved by initially bubbling compressed air through 1 liter of distilled water to remove impurities and then through 3 liters of distilled water maintained at 40° C. Probe 12 was placed in the chamber and face 14 was coated with a film of the mineral oil to be tested, which was then allowed to drain down the slope of the face for 5 minutes. In some of the tests, antifreeze at 15° C. was then circulated through hollow tube 28, causing condensation directly on the lubricant film. In other of the tests probe 12 was left uncooled.

Figure 4A:
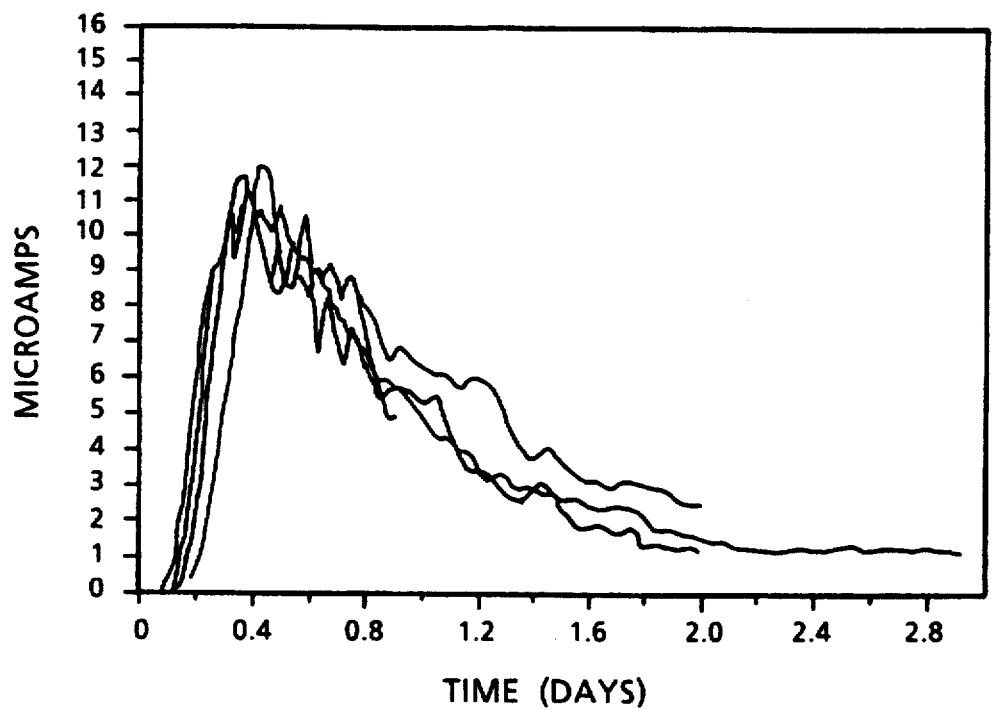
FIG. 4a is a plot of corrosion current versus time obtained from using the invention with a cooled probe.
Figure 4B:
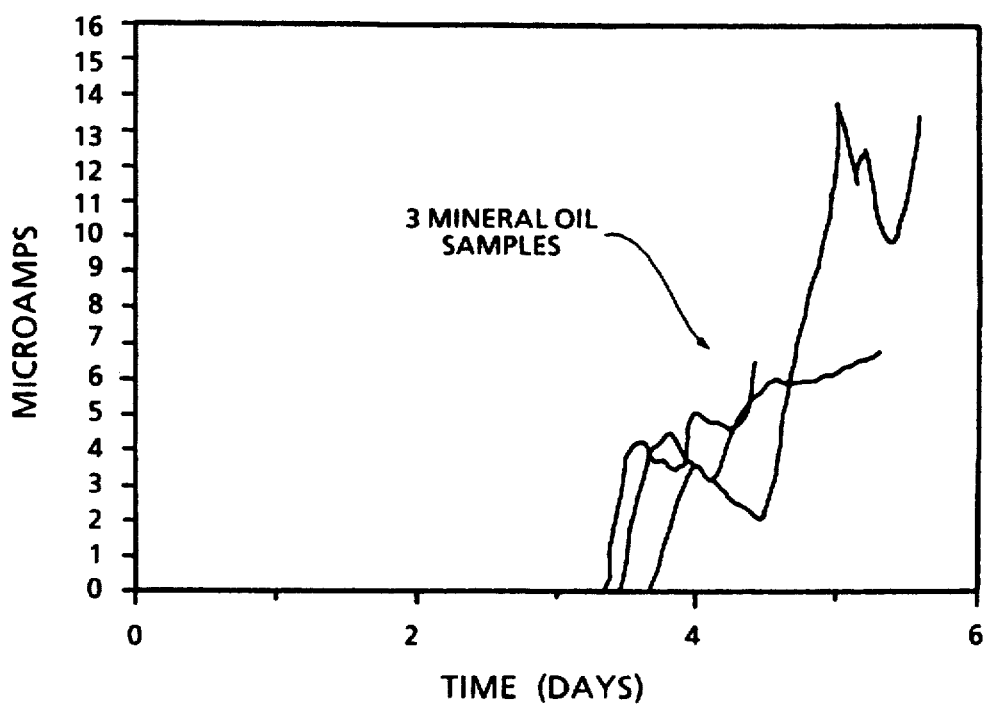
FIG. 4b is a plot of corrosion current versus time obtained from using the invention with an uncooled probe.

The results obtained using corrosion monitoring apparatus 10 to test the various mineral oils are represented in FIGS. 4a and 4b, which show plots of the corrosion current versus time for the cooled and uncooled probe, respectively. A comparison of the two figures shows that using the cooled probe not only accelerates the test, but also reduces corrosion current transients, as represented by the fewer number of peaks and valleys in the cooled probe curves. This reduction in current transients allows for better reproducibility of test results. This difference in performance could be due to the fact that the film of condensation relied upon when using the uncooled probe results from droplets of condensation which fall from the lid of the environmental chamber, providing an uneven and inconsistent film, whereas the cooled probe causes an even film of condensation to form directly on face 14.

Some of the many advantages and novel features of the invention should now be readily apparent. For instance, an apparatus and a method have been provided for quantitatively measuring the corrosion-inhibiting ability of thin films of materials. The corrosion-monitoring apparatus of the present invention can detect corrosion before any visible signs thereof are present. Additionally it has good reproducibility and high sensitivity, being able to detect slight changes in corrosion rates. Furthermore, the present invention does not require an aggressive artificial environment to produce a measurable amount of oxidation or corrosion and can therefore measure corrosion in more realistic environments that are reflective of where the material is actually used. Furthermore, it simulates the actual drainage conditions of lubricants in use with aircraft turbine engine bearings, for example.

Other embodiments and modifications of the present invention may readily come to those of ordinary skill in the art having the benefit of the teachings presented in the foregoing description and drawings. Therefore, it is to be understood that the present invention is not to be limited to such teachings presented, and that such further embodiments and modifications are intended to be included within the scope of the appended claims.

What is claimed is:

1. Apparatus for monitoring the corrosion beneath a thin film of lubricant exposed to a humid environment having a known dew point temperature comprising:
   a matrix of insulating material having an essentially flat sensitive bevelled face oriented at an angle with the horizontal ranging from 10 to 80 degrees, on which the thin film of lubricant is to be disposed;
   a plurality of electrically isolated surface areas of anodic material disposed on the sensitive face;
   a plurality of electrically isolated surface areas of cathodic material disposed on the sensitive face in alternating relationship with the anodic surface areas;
   a first conducting means connected to each of the anodic surface areas;
   a second conducting means connected to each of the cathodic surface areas; and
   means electrically connected to said first and said second conducting means for measuring the current generated therebetween, the current being the corrosion current generated at the sensitive face beneath the thin film of lubricant.

2. The apparatus of claim 1 wherein the angle of the sensitive face with the horizontal ranges from 50 to 70 degrees.

3. The apparatus of claim 1 wherein the angle of the sensitive face with the horizontal is approximately 60 degrees.

4. The apparatus of claim 1 wherein the anodic and the cathodic surface areas are substantially long and narrow in shape.

5. The apparatus of claim 4 wherein the anodic and the cathodic surface areas are substantially parallel to each other.

6. The apparatus of claim 5 wherein the anodic and the cathodic surface areas are substantially parallel to the horizontal.

7. The apparatus of claim 1 further comprising means operatively connected to the sensitive face for cooling the face to a temperature below the dew point temperature such that condensation forms on the thin film of lubricant.

8. Apparatus for monitoring the corrosion beneath a thin film of lubricant exposed to a humid environment having a known dew point temperature, comprising:
   a matrix of insulating material having a substantially horizontal face and an essentially flat sensitive face adjacent thereto and forming an angle therewith ranging from 10 to 80 degrees, on which the thin film of lubricant is to be disposed;
   a plurality of plates of an anodic material embedded within said matrix and positioned such that each of said anodic plates is surrounded by said matrix with one edge forming part of the sensitive face;
   a plurality of plates of a cathodic material embedded within said matrix in alternating relationship with the anodic plates and positioned such that each of said cathodic plates is surrounded by said matrix with one edge forming part of the sensitive face;
   means operatively connected to the sensitive face for cooling the face to a temperature below the dew point temperature such that condensation forms on the thin film of lubricant;
   a first conducting means connected to each of said anodic plates;
   a second conducting means connected to each of said cathodic plates; and
   means electrically connected to said first and said second conducting means for measuring the current generated therebetween, the current being the corrosion current generated at the sensitive face beneath the thin film of lubricant.

9. The apparatus of claim 8 wherein the angle between the horizontal face and the sensitive face ranges from 50 to 70 degrees.

10. The apparatus of claim 8 wherein the angle between the horizontal face and the sensitive face is approximately 60 degrees.

11. The apparatus of claim 8 wherein said anodic and cathodic plates are substantially parallel to each other.

12. The apparatus of claim 11 wherein said anodic and cathodic plates are substantially parallel to the horizontal face.

13. The apparatus of claim 8 wherein the distance on the sensitive face between adjacent ones of said anodic and cathodic plates is less than 1 mm.

14. The apparatus of claim 8 wherein the distance on the sensitive face between adjacent ones of said anodic and cathodic plates is approximately 0.8 mm.

15. The apparatus of claim 8 wherein said cooling means comprises a hollow tube embedded in said matrix for carrying a liquid at a predetermined temperature below the dew point temperature.

16. The apparatus of claim 8 wherein said anodic and cathodic materials have a large electrochemical potential difference therebetween.

17. The apparatus of claim 8 wherein said anodic material is an iron alloy and said cathodic material is a copper alloy.

18. The apparatus of claim 8 wherein the insulating material is resistant to water penetration and forms a strong bond with said anodic and cathodic materials.

19. The apparatus of claim 8 wherein said matrix comprises an epoxy.

20. The apparatus of claim 19 wherein said matrix further comprises Teflon plates embedded in said epoxy and positioned in alternating relationship with said anodic and cathodic plates.

21. The apparatus of claim 8 wherein said matrix comprises epoxy-impregnated cloth.

22. The apparatus of claim 21 wherein said matrix further comprises Teflon plates embedded in said epoxy-impregnated cloth and positioned in alternating relationship with said anodic and cathodic plates.

23. A method for monitoring the corrosion beneath a thin film of lubricant comprising the steps of:
   providing an essentially flat sensitive bevelled face oriented at an angle with the horizontal ranging from 10 to 80 degrees and having disposed thereon a plurality of electrically isolated anodic and cathodic surface areas in an alternating relationship;
   coating the sensitive face with the thin film of lubricant and allowing the lubricant to drain therefrom;
   exposing the coated face to a humid environment having a known dew point temperature;
   cooling the coated face to a temperature below the dew point temperature, causing condensation to form on the thin film of lubricant; and measuring the current generated between the anodic and cathodic surface areas, the current being the corrosion current generated at the sensitive face beneath the thin film of lubricant.

24. The method of claim 23 wherein the angle of the sensitive face with the horizontal ranges from approximately 50 to 70 degrees.

25. The method of claim 23 wherein the angle of the sensitive face with the horizontal is approximately 60 degrees.

* * * * *